United States Patent [19]

Fleury, Jr.

[11] Patent Number: 4,475,679

[45] Date of Patent: Oct. 9, 1984

[54] MULTI-STAPLE CARTRIDGE FOR SURGICAL STAPLERS

[76] Inventor: George J. Fleury, Jr., 1005 Abbey Way, McLean, Va. 22101

[21] Appl. No.: 291,086

[22] Filed: Aug. 7, 1981

[51] Int. Cl.³ ............................................. A61B 17/04
[52] U.S. Cl. .................................. 227/19; 128/334 R; 227/DIG. 1; 206/339
[58] Field of Search .......... 128/334 R, 334 C, 329 R, 128/330; 227/DIG. 1, 19; 206/438, 339

[56] References Cited

U.S. PATENT DOCUMENTS

| | | | |
|---|---|---|---|
| 3,080,564 | 3/1963 | Strekopitov et al. | 128/334 R |
| 3,275,211 | 9/1966 | Hirsch et al. | 227/124 |
| 3,564,582 | 2/1971 | Wai | 128/334 C X |
| 3,606,888 | 9/1971 | Wilkinson | 128/334 R |
| 4,111,206 | 9/1978 | Vishnevsky et al. | 128/334 R X |
| 4,310,115 | 1/1982 | Inoue | 128/334 R X |

FOREIGN PATENT DOCUMENTS 527365  7/1956  Canada ........................ 128/329 R Primary Examiner—Michael H. Thaler
Attorney, Agent, or Firm—Ziems, Walter & Shannon

[57] ABSTRACT

A multi-staple cartridge for surgical staplers in which individual staples are retained and driven by separate but commonly actuated staple retaining units. Each of the units includes a movable staple carrier and a staple driving head. All units are actuated by a cartridge contained driving press so that the driving head and carrier are first moved together under a limited or yieldable force transmitting means tending to retain them in their initial relative position. The force transmitting means operative between the common driving press then advances the driving head relative to the carrier to set the staple. Final movement of the carrier and driving head is by direct abutting engagement with the driving press for all staples not previously clinched by the force of the yieldable force transmitting means. Tissue thickness variation is thus accommodated by each individual staple.

15 Claims, 14 Drawing Figures

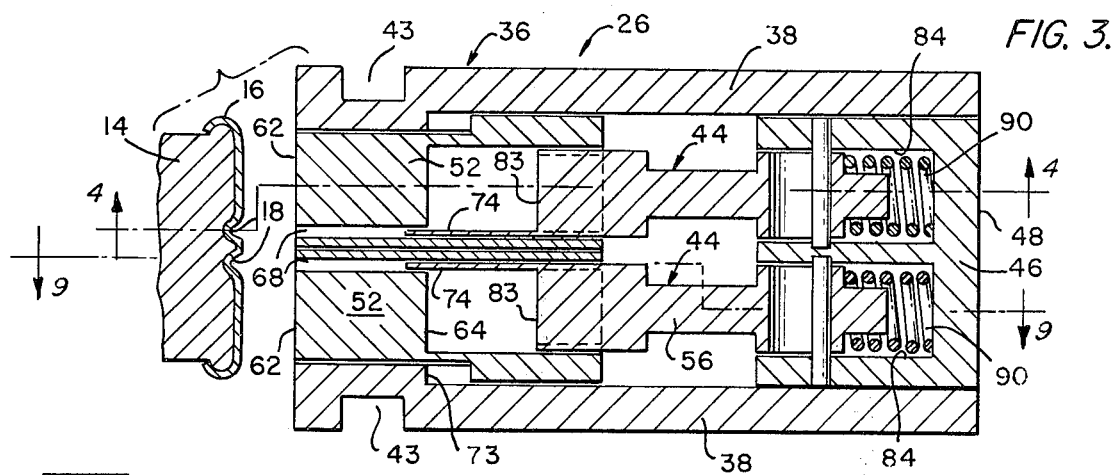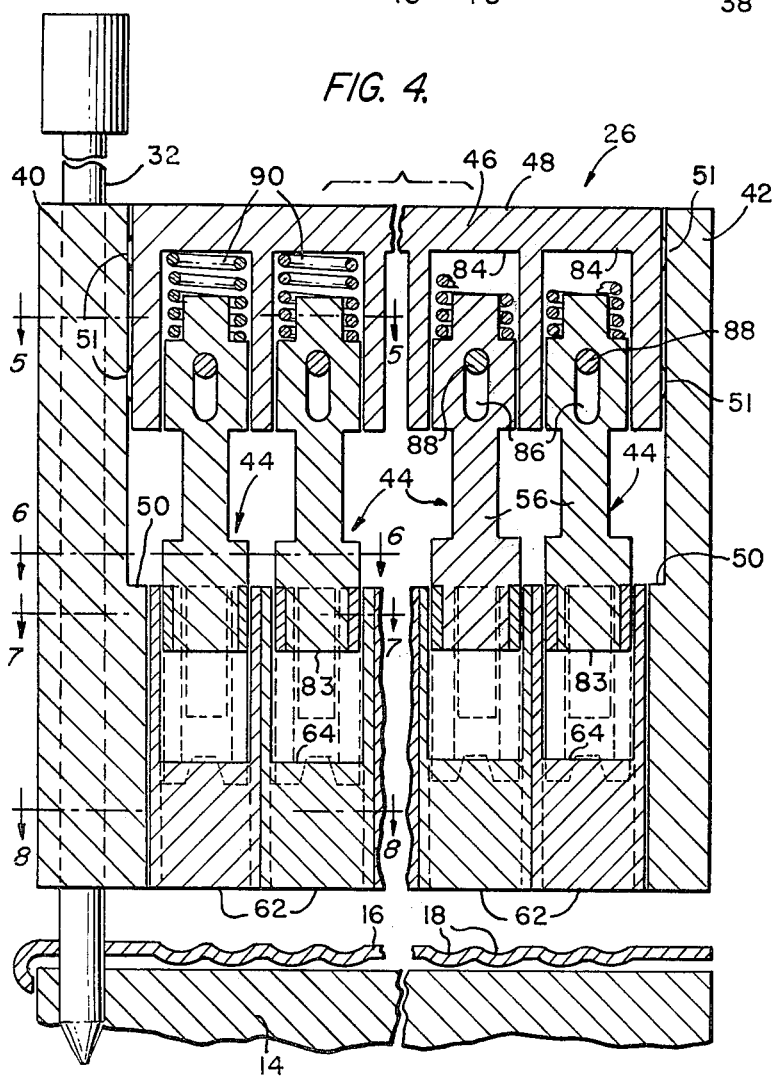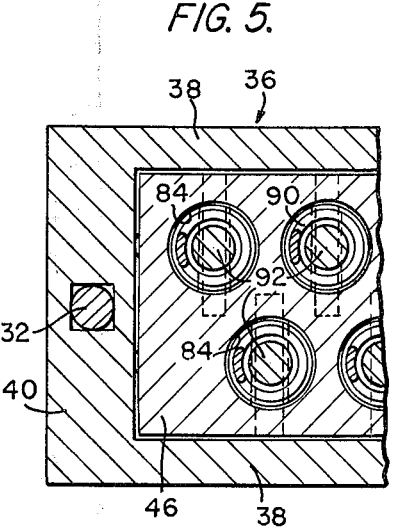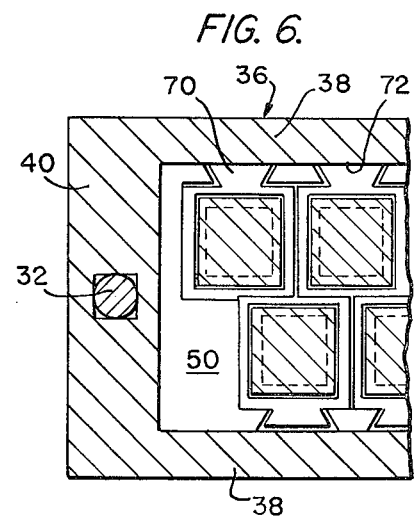

MULTI-STAPLE CARTRIDGE FOR SURGICAL STAPLERS

BACKGROUND OF THE INVENTION

This invention relates to surgical staplers and more particularly, it concerns an improved multi-staple cartridge for such staplers by which uniform tissue compression and staple driving forces are assured for individual staples irrespective of variations in tissue thickness in the area of multiple staple application.

U.S. Pat. Nos. 3,080,564-Strekopitov et al and 3,275,211-Hirsch et al exemplify basic structural and functional characteristics of surgical staplers currently in use. In staplers of the general type disclosed in these patents, a multi-staple cartridge is adapted to be retained along the face of a head jaw parallel to and movable in relation to an anvil carried along the face of another jaw of the stapler. In use, tissue to be stapled is received between the jaws which are then adjusted to compress the tissue between the leading face of the staple cartridge and the anvil. Thereafter, the stapler is actuated to drive all staples in the cartridge simultaneously through the tissue and against the anvil for deflecting or bending the projecting legs of each staple inwardly and back into the tissue so that each staple so placed assumes a configuration resembling a "B".

The distance between the face of the cartridge and the anvil after tissue compressing adjustment of the stapler jaws falls within a range dictated by staple size. In particular, each staple size has a safe working range which represents the difference between the maximum and minimum separation of the anvil and cartridge face which will insure proper bending of the staple legs to secure the stapled tissues. The maximum safe distance of separation is determined by the least amount of staple leg bending needed for staple retention of the tissues whereas the minimum safe distance of separation is determined by the ability of the staple to retain the tissues in adequate proximity for healing. The specific distance of jaw face separation within the safe working range of a particular staple size is largely a matter of judgment by the surgeon though devices are available for measuring the combined thickness of tissues to be stapled.

While the present state of surgical stapler development accommodates a range of tissue thickness for a specific staple size, there remains no provision for variation in the thickness of tissues over the length of a line (or double line) of staples inserted simultaneously from a single cartridge. In certain organs, such as the large intestine, tissue thickness may vary considerably over the length of a multi-staple cartridge face. Although the thickest tissue may fall within the safe working range of the size of staples in a given cartridge, the legs of all such staples will be bent to the same configuration because of the common distance of separation between the stapler jaws at the time of final staple application. As a result, staples applied in relatively thin sectors of tissue will be too loose to completely seal the tissue, can lead to bleeding, leakage and other complications. There is a need therefore for increased accommodation of tissue thickness variation in multi-staple surgical staplers.

SUMMARY OF THE INVENTION

In accordance with the present invention, a multi-staple cartridge is provided for surgical staplers and by which the degree of tissue compression as well as the extent to which each staple is driven toward the anvil is determined separately for each individual staple in the multi-staple cartridge. This capability, in turn, is achieved with a cartridge having a frame adapted to be secured in the head of the stapler and a driving press supported by the frame for movement toward the anvil, for example, by providing a plurality of individual staple retaining units in an orientation resulting in a staple line pattern comparable to that of existing staple cartridges. Each of the individual units includes a staple carrier movably supported from the cartridge frame and having a staple receiving chamber opening through a working end surface facing in the direction of the anvil. Each unit further includes a staple driving head and force transmitting means operative primarily for transmitting to the staple driving head of each unit a substantially constant, predetermined force upon actuating movement of the driving press which is common to all units, and secondarily, for causing movement of the carrier with the staple driving head. In operation, the working end surface of each unit carrier is advanced toward the anvil in compressing engagement with the tissue to be stapled. The individual end faces will be retained against the tissue by the force transmitting means. Upon further movement of the driving press, the force transmitting means will cause the driving head of each unit to advance the staple therein through the tissue and against the anvil. A positive follow-up system is provided so that none of the individual staples is driven through less than the maximum safe working range of the common length or size of all staples contained in the cartridge.

A principal object of the present invention is, therefore, the provision of an improved multi-staple cartridge for surgical staplers which compensates automatically for variation in tissue thickness throughout the length of multiple staple application. Other objects and further scope of applicability of the present invention will become apparent from the detailed description to follow taken in conjunction with the accompanying drawings in which like parts are designated by like reference numerals.

BRIEF DESCRIPTION OF THE DRAWINGS

FIG. 3 is a cross-section on line 3—3 of FIG. 1;

FIG. 4 is a fragmentary cross-section on line 4—4 of FIG. 3;

FIG. 5 is a fragmentary cross-section on line 5—5 of FIG. 4;

FIG. 6 is a fragmentary cross-section on line 6—6 of FIG. 4;

DETAILED DESCRIPTION OF THE PREFERRED EMBODIMENTS

Figure 1:
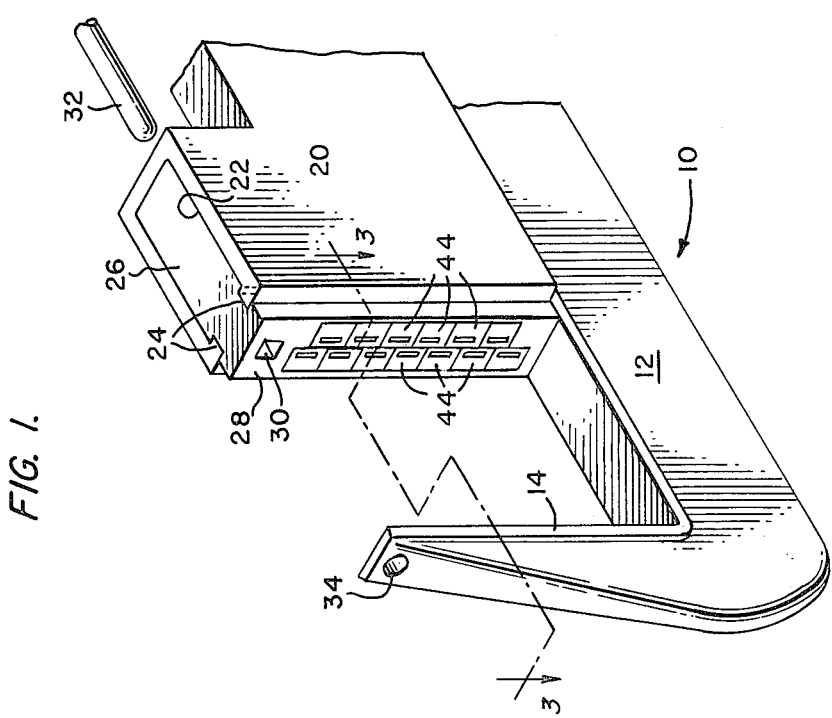
FIG. 1 is a fragmentary perspective view illustrating a portion of a surgical stapler equipped with the cartridge of the present invention.
Figure 7:
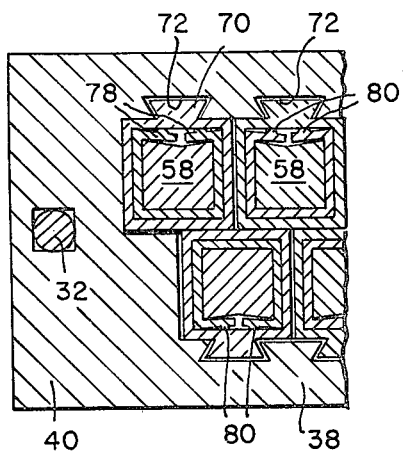
FIG. 7 is a fragmentary cross-section on line 7—7 of FIG. 4.
Figure 8:
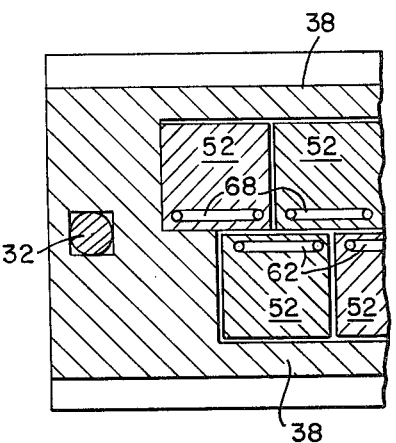
FIG. 8 is a fragmentary cross-section on line 8—8 of FIG. 4.

In FIG. 1 of the drawings, the jaw portion only of a surgical stapler is designated generally by the reference numeral 10 and shown to include a beam 12 from which a fixed jaw 14 projects perpendicularly. Although not visible in FIG. 1, the jaw 14 conventionally supports an anvil plate 16 (FIG. 3 for example) having two rows or lines of staggered staple clinching anvil recesses 18. Adjustably supported for movement along the beam toward and away from the jaw 14 is a cartridge head 20. The head 20 is provided with a generally rectangular cartridge receiving chamber 22 having an opening at its front edge which is bounded on two sides by a pair of inwardly turned flange portions 24. A cartridge 26 is shown mounted in the head 20 and although incorporating features of the present invention which will be described in detail below, is conventional to the extent that it includes a front working face 28 and an aperture 30 through which a retaining pin 32 may be inserted. The retaining pin 32 is a conventional adjunct to such staplers and when inserted through the aperture 30 and an aperture 34 in the jaw, functions to retain the assembly of the cartridge 26 in the head 20, of the anvil plate 16 and the fixed jaw 14 and additionally closes the space between the anvil and the working face 28 of the cartridge. Although not shown in the drawings, the stapler conventionally includes a firing mechanism as well as means for adjusting the spacing of the head 20 relative to the fixed jaw 14. Reference may be made to the aforementioned U.S. patents for an exemplary disclosure of components conventionally included in surgical staplers and not shown in the drawings.

As may be seen most clearly in FIGS. 3 and 4 of the drawings, the cartridge 26 in the illustrated embodiment includes a generally rectangular frame 36 having opposite side walls 38 connected by end walls 40 and 42. The side walls 38 include external grooves 43 to receive the inwardly turned flanges 24 on the stapler head 20. Also it will be noted that the pin receiving aperture 30 extends throughout the length of and is confined entirely within the end wall 40.

The frame 36 circumscribes a plurality of individual staple retaining units, each of which is designated generally by the reference numeral 44 in FIGS. 3 and 4 of the drawings. Although the units 44 will be described in more detail below, it will be noted in FIGS. 3 and 4 that the units are presented at one end through the front or working face 28 of the cartridge 26 and that each unit extends at its other end to a common actuating means in the form of a driving press 46 having a striking face 48 and reciprocably mounted for movement in the frame 36 between a retracted position shown in FIG. 3 and 4 and a maximum depressed position delimited by an abutment shoulder 50 or equivalent inside the end walls 40 and 42 as shown in FIG. 4, for example. The position of the press 46 relative to the frame 36 may be maintained, in the absence of an applied external force, by frictional engagement of convex protuberances 51 with interior surfaces of the end walls 40 and 42.

Figure 2:
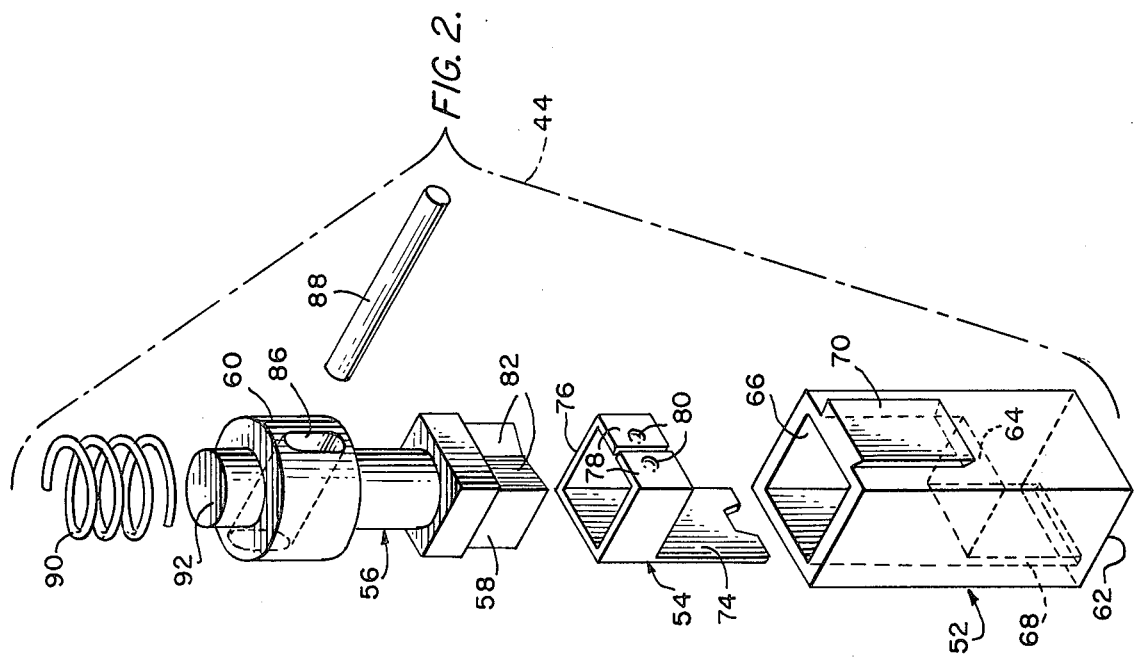
FIG. 2 is an exploded perspective view illustrating components of a staple unit in the cartridge of the present invention.

Exemplary components for each of the staple retaining units 44 are shown in FIG. 2 to include a generally rectangular staple carrier 52 and a staple driving head 54 carried by plunger 56 having a generally rectangular head mount 58 at one end and a cylindrical body portion 60 at the other end. The carrier 52 has a front face 62 spaced from the floor 64 of a rectangular head receiving chamber 66. A staple retaining slot 68 extends between and opens through the working face 62 and the chamber floor 64. Each staple carrier 52 is supported slidably from the cartridge frame 36 for relative movement in a direction normal to the front face 62 thereof by virtue of a dovetail-like tenon 70 on the exterior of each carrier 52 being slidably engaged in a complementary undercut groove 72 (FIG. 6) in the side walls 38 of the frame 36. The grooves 72 end at shoulder-like floors 73 to limit movement of the carriers 52 in a direction out of the frame 36.

The staple driving head 54 of each unit 44 includes a plate like striker 74 projecting from a rectangular mounting portion 76 which, in the embodiment of FIGS. 1–9, is open on the side opposite from the striker 74 to define a pair of leaf spring segments 78 having convex projections 80 formed thereon. The projections 80 engage the interior surfaces of the chamber 66 and provide a yieldable force transmitting means in the form of a frictional drag by which relative movement of the head 54 in the carrier 52 is restrained. The rectangular portion 76 of the driving head 54 is dimensioned to fit about the rectangular mount 58 of the plunger 56, one side of the mount 58 being provided with angled or chamfered surfaces 82 so that flexure of the spring segments 78 is unimpeded. The rectangular mount 58 is preferably of the same length as the mounting portion 76 so that together, these components present a flush base 83 (FIGS. 3 and 4) engageable with the floor 64 to limit one direction of relative movement between the driving head 54 and the carrier 52 of each unit 44. Also it is to be noted that the length of the striker 74, or the distance between the distal free end thereof and the flush base 83 of the mount 58 and frame 76 is substantially equal to the distance between the face 62 and the floor 64 in each carrier 52.

The cylindrical portion 60 of each plunger 56 is slidably received within cylindrical chambers 84 (FIGS. 3–5) in the driving press 46. Movement of the plungers 56 relative to the press 46 is restrained by the length of slots 86 in the cylindrical body portion 60 and pins 88 extending to be anchored in the driving press 46. Compressible elastic means in the form of springs 90, in this embodiment, extend between the end of each cylindrical body portion 60 and the bottom of the cylindrical chambers 84 in the driving press 46. The springs 90 circumscribe an abutment stud 92 on the end of each plunger 56 and function as a force transmitting means by which actuating movement of the driving press is transmitted as driving movement of the driving head 54 of each unit 44.

Figure 9A:
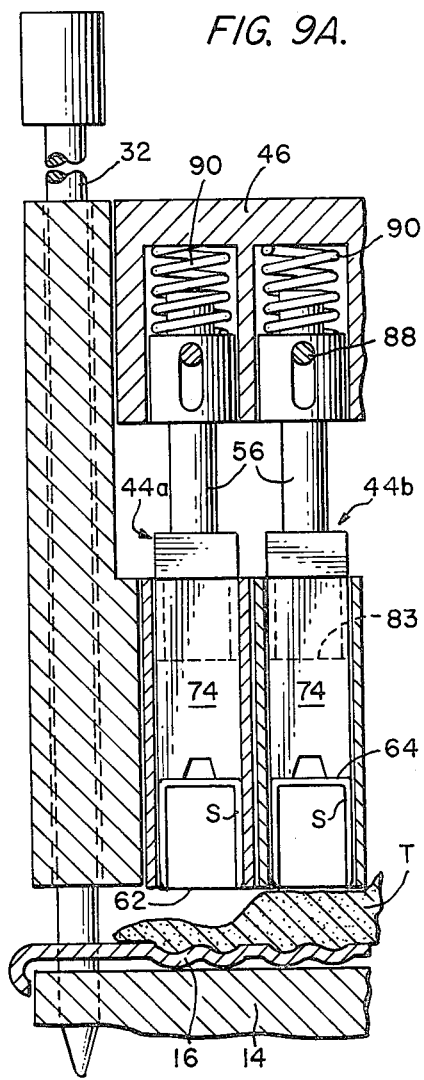
FIGS. 9A-9C are fragmentary cross-sections on line 9—9 of FIG. 3 and illustrating components in different operating positions during operation.
Figure 9B:
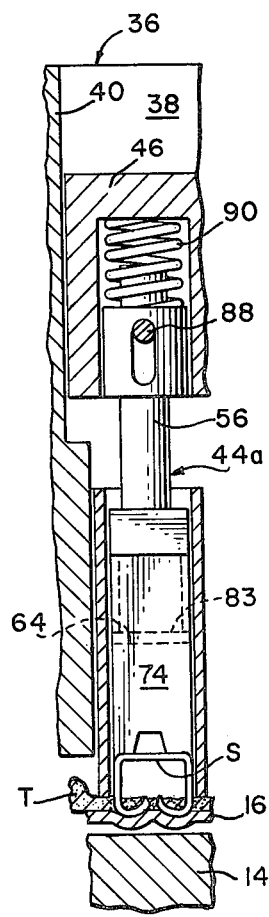
Figure 9C:
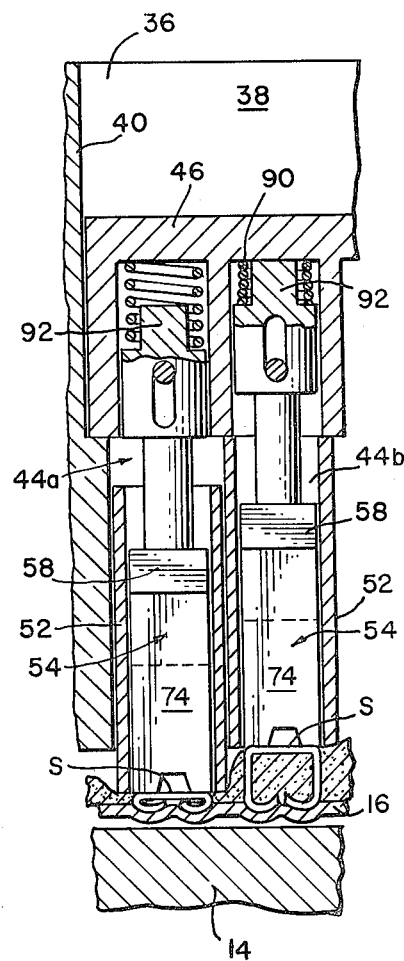

Operation of a surgical stapler equipped with the cartridge 26 of the present invention may be understood by reference to FIGS. 9A–9C of the drawings. In these figures, two staple units are depicted in various operating conditions and designated by the reference numerals 44a and 44b. Each unit contains a staple S of conventional design and loaded in the slot 68 of each carrier 52 respectively. Also the cartridge is shown in these figures to be positioned so that its working face 28 is closed against tissue T, to be secured by stapling, and in working relationship with the anvil 16. In this respect, the appropriate spacing between the face 28 and the anvil will be effected by movement of the head 20 toward the anvil 16 and against the tissue T so that the distance between the face 28 and the anvil 16 will correspond to the maximum safe distance of separation as determined by the leg length of the particular staples S with which the cartridge 26 is loaded.

The aforementioned determination of the spacing between the face 28 and the anvil 16 differs from a corresponding adjustment in conventional surgical staplers where head adjustment within a limited permissible range of such adjustment is determined subjectively or by "feel" on the part of the surgeon using the stapler. Because the leg length and correspondingly, the maximum safe working distance for the staples loaded into a particular cartridge is a known finite value, and because of the operation of each unit 44 to be described, preliminary positioning of the head 20 using the cartridge of the present invention may be effected in increments corresponding to staple size only. The positioned increments, in turn, may be established mechanically by means which, though not shown in the drawings, could include detents, pawl and ratchet mechanisms, abutment stops and the like which eliminate all guess-work in attaining the proper working position of the head 20.

As shown in FIG. 9A, the tissue underlying the unit 44a is considerably thinner than the tissue underlying the unit 44b. Positioning of the head 20 may involve a compression of the thicker regions of tissue. Also it should be borne in mind that movement of the head 20 will not in any way have an effect on the relative positions of components in each staple unit 44.

After positioning the head to attain the proper distance of separation between the anvil 16 and the face 28, the stapler may be fired such that a push rod (not shown) moves into engagement with the striker face 48 of the driving press 46 which is common to all units 44. Upon initial depressing movement of the driving press 46, the staple carriers 52 will be moved in the direction of the anvil 16 so that the working faces 62 thereof engage the tissue T. The force acting to move the carrier 52 against the tissue will be determined by the drag exerted on the carrier 52 by the projections 80 on the spring segments 78. Movement of the carriers under that force, however, will be impeded by pressure on the tissue acting over the full area of each of the end faces 62 which areas are large relative to the end faces of each of the strikers 74. By appropriate design of this drag in combination with the yieldability or compression strength of the spring 90 for each unit 44, compression of the spring 90 during this period will be minimal. Further actuating movement of the driving press 46 will overcome the frictional retention between the driving heads 54 and the carriers 52 causing the striker plate 74 to advance the respective staples S through the tissue T and against the anvil 16. This condition is illustrated in FIG. 9B. The force with which the staple is so driven against the anvil initially is solely the force transmitted from the driving press 46 through the respective springs 90, but concentrated at the relatively small end area of each striker 74 so that the driving pressure on each staple is higher than the tissue pressure acting to hold the carriers 52 against movement. The force transmitted through the springs 90 is preferably a constant force throughout compressive foreshortening of the springs 90 or as nearly constant as possible within practical limits of compression spring design. Moreover, the magnitude of the spring force is selected so that it is adequate, in itself, to drive each staple through the tissue T and completely clinch the staple legs.

It will be noted from FIG. 9C that the staple retained by the unit 44a is completely driven through the thin section of the tissue T with minimal deformation or compression of spring 90. In both units, however, the respective driving heads 54 and carriers 52 have reached the limit of relative movement by engagement of the base 83 of the plunger mount 58 with the chamber floor 64. As a result, and irrespective of variation in tissue thickness, final clinching of each staple is accompanied by a compression of tissue in the region of the respective staples, determined by the area of each end surface 62, so that positive proximity of tissue retained by each staple is assured.

In the case of the unit 44b, the top of the abutment stud 92 is in engagement with the base of the chamber 84. This condition is the result of resistance by the tissue under the unit 44b to pressure exerted by the face 62 on the carrier 52 of that unit, causing abutment of the base 83 on the plunger 56 with the floor 64 in the carrier and compressive foreshortening of the spring 90 until the stud 92 engages the base of the chamber 84 in the driving press 46. In FIG. 9C, therefore, where the driving press 46 is shown in its most advanced position, final staple driving is positive and not through the yieldable force transmitting means. As a result of this condition, all staples will be driven at least to the extent illustrated under the unit 44b in FIG. 9C. Yet none will be driven beyond the tissue surface engaged by the end face 62 of the carrier 52 for each unit.

Figure 11:
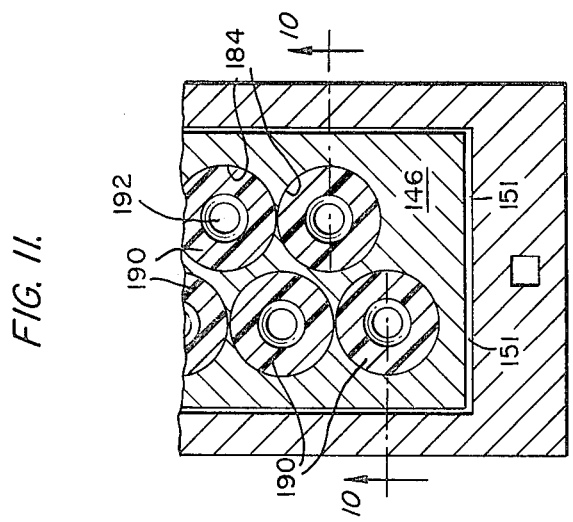
FIG. 11 is a fragmentary cross-section on line 11—11 of FIG. 10.
Figure 10:
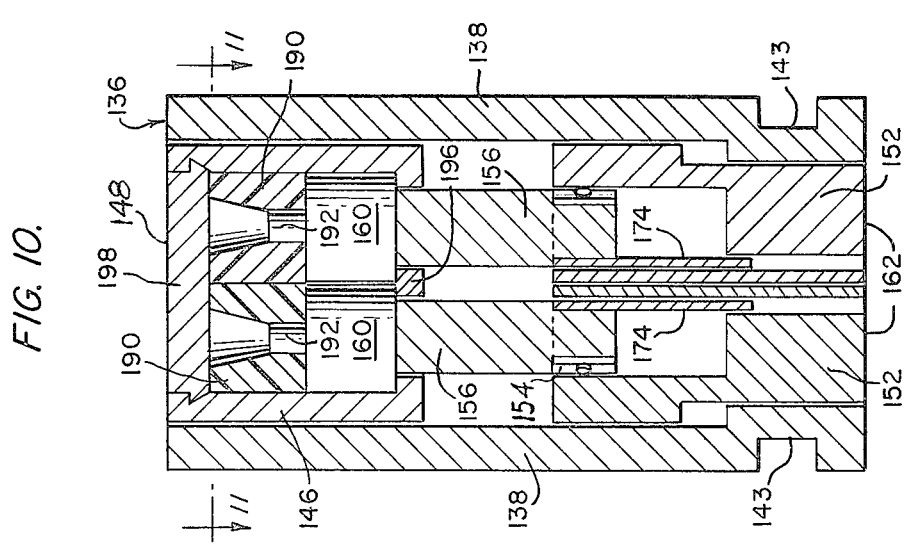
FIG. 10 is a cross-section on line 10—10 of FIG. 11, similar to FIG. 3, but illustrating a modified embodiment of the present invention.

In FIGS. 10 and 11 of the drawings, an alternative embodiment of the staple cartridge of the present invention is shown in which components previously identified and serving corresponding functions are designated by the same reference numerals but to which the number 100 has been added. Thus in FIG. 10, the cartridge 126 is again provided with a rectangular frame 136 in which the upper ends of the unit plungers 156 extend within a driving press 146 having a striking surface 148. In this embodiment, however, the force transmitting means acting between the press 146 and the plungers 156 is in the nature of a compressible annulus 190 of elastomeric material and like the compression springs 90 of previously described embodiment, circumscribe abutment studs 192 at the top of each plunger 156.

The embodiment of FIG. 10 also incorporates an assembly facilitating advantage by comparison to the embodiment of FIGS. 1-9. In particular, the plungers 156 are provided with enlarged heads 160 at their upper ends and depend with uniform cross-sectional dimension the same as the cross-sectional dimension of the driving head 154. As such, the plungers 156 with the driving heads 154 attached, may be inserted downwardly through chamber 184 in the driving press 146 and restricted from downward movement in relation to the driving press 146 by a bottom wall 196 therein. After so inserting the plungers 156 and the force transmitting means, in the form either of the springs 90 or of the elastomeric annuli 190, a cap 198 is snap fit into the driving press 146 to complete the assembly. Thus it will be appreciated that in the embodiment of FIG. 10, the assembly of the cartridge is simplified by avoidance of the pins 88 without loss of operating capability.

Figure 12:
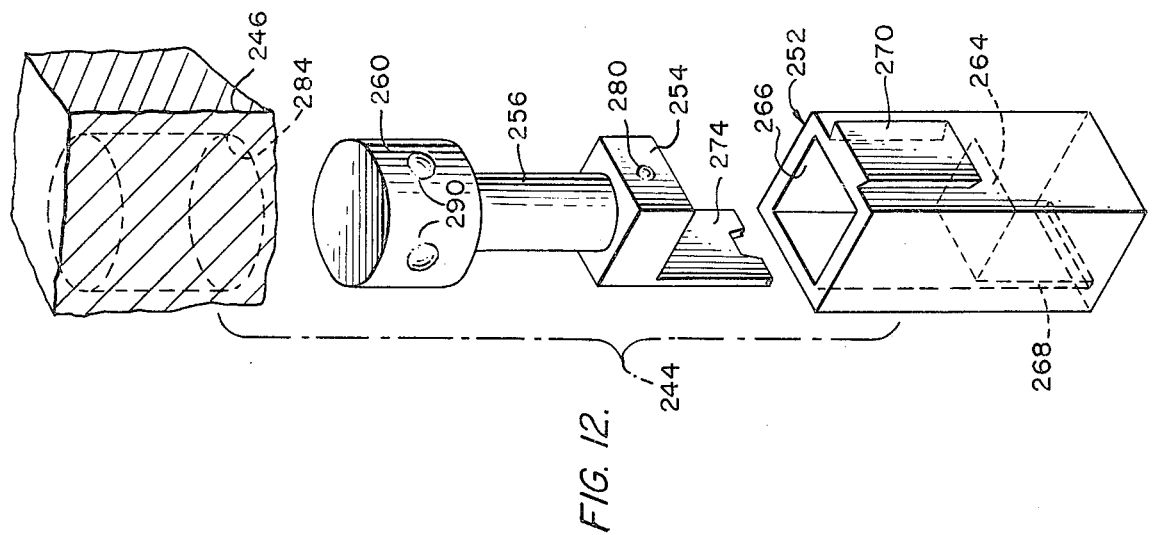
FIG. 12 is an exploded perspective view of a further modified embodiment of the invention.

A further embodiment of the invention is illustrated in FIG. 12 of the drawings where components corresponding to parts previously identified are designated by reference numerals having the same tens and digits numbers but in a two hundred series. Thus in FIG. 12, the organization of the carrier 252, plunger 256 and driving press 246 applicable to each individual unit 244 is illustrated. In this instance, however, the plunger 256 is integrated with the staple driving striker plate 274. Also, the springs 90 of the embodiment illustrated in FIGS. 1–9 are replaced by a plurality of projections 290 on the periphery of the enlarged head 260 of the plunger. The projections 290 are arranged to engage frictionally the inner cylindrical surfaces of the chambers or bores 284 in the driving press 246. As in the previous embodiment, a projection 280 on the rectangular base 254 of the plunger 256 frictionally retains the plunger and the carrier 252. This embodiment has the advantage of enhanced simplicity and relies exclusively on frictional drag to provide the force transmitting means between the plunger 256 and both the carrier 252 and the press head 246.

In light of the foregoing description of alternative embodiments, it will be appreciated that the invention may be embodied in diverse structural forms without departure from the basic staple placing function of the invention. Additional variations and/or modifications will be apparent to those skilled in the art and are contemplated. For example, in each of the disclosed embodiments, the respective staple driving units are designed to accommodate single staples. It is contemplated that in some applications, each unit might be designed to retain and drive two or more staples, the particular number of staples in that instance depending on anticipated tissue thickness variation in the region of staple application. Also, the several embodiments illustrated are applicable to the placement of linear rows of staples. The invention is equally applicable to stapler systems in which one or more concentric rings of staples are placed. Furthermore, in the illustrated embodiments, the staple cartridge is adapted to be removably secured in a conventional staple gun. Disposable surgical stapling guns are available, however, where the cartridge is integrated with the gun. The invention is equally applicable to such disposable staplers merely by an integration of the cartridge body or frame 36 with the equivalent of the head 20 of such a stapler. Finally, it is contemplated that the various components may be formed from several diverse materials. Although such components as the spring 90 and the staple driving head 54 in the embodiment of FIGS. 1–9 might be formed of metal such as stainless steel whereas other components could be molded of plastic. Alternatively, all components might be formed of plastic material without departure from the invention.

In light of the foregoing description and accompanying drawings, it will be appreciated that a highly effective surgical stapling apparatus is provided and that while preferred embodiments have been described and illustrated, variations may be made in the embodiments illustrated and described herein without departure from the invention. Accordingly, it is expressly intended that the foregoing description and accompanying drawings are illustrative only, not limiting, and that the true spirit and scope of the present invention will be determined by reference to the appended claims.

I claim:

1. In a surgical stapler having an anvil for clinching a plurality of staples simultaneously, the improvement comprising:

means defining a plurality of staple retaining units, each of said units comprising an independently movable staple carrier having an end surface facing in the direction of and movable toward said anvil, and a staple driving head movable relative to said carrier; and means for effecting simultaneous staple driving operation of said units to cause the carrier end surface of each of said units to move toward said anvil followed by movement of the staple driving head relative to the carrier of each unit, respectively;

said end surface having an area larger than the area to which the force of said driving head is applied to a staple, thereby to impede movement of said carrier under a pressure imposed by said end surface on tissue overlying said anvil, which pressure is lower than the driving pressure of said driving head against a staple.

2. The apparatus recited in claim 1, wherein said last-mentioned means comprises actuating means common to all of said units and force transmitting means for operatively connecting said actuating means to the carrier and to the driving head of each of said units.

3. The apparatus recited in claim 2, wherein said force transmitting means is effective to move the carrier and the driving head of each of said units under respective predetermined and substantially constant driving forces.

4. The apparatus recited in claim 3, wherein the driving force acting on said driving head in each unit is larger than the driving force acting on said carrier in each unit.

5. The apparatus recited in claim 3, wherein said actuating means comprises a driving press movable in relation to all of said units.

6. The apparatus recited in claim 5, wherein said force transmitting means comprises compressible elastic means between said driving press and the staple driving head of each of said units, and means to provide a friction drag between the driving head and the carrier in each of said units.

7. The apparatus recited in claim 5, wherein said force transmitting means comprises means to provide a frictional drag between said driving press and said staple driving head and between said driving head and said carrier.

8. The apparatus recited in either of claims 5, 6, or 7, including means to provide a direct connection of said driving press with the driving head and carrier of each unit after predetermined relative movement between said driving press and said driving head and between the driving head and the carrier of each unit, respectively.

9. The apparatus recited in claim 8, wherein said staple retaining carrier of each unit comprises means to retain a single staple.

10. A multi-staple cartridge for surgical staplers having cartridge mounting head and an anvil, said cartridge comprising:

a frame adapted to be secured in the cartridge head of the stapler;

a driving press supported by said frame for movement toward the anvil; and a plurality of staple retaining units carried by said frame between said driving press and anvil, each of said units comprising a staple carrier having an end surface facing in the direction of the anvil, a staple receiving chamber opening through said end surface and means supporting said carrier for movement in the direction of the anvil; a staple driving head; and force transmitting means operable between said driving press and said driving head on the one hand and said driving head and said carrier on the other hand;

said end surface having an area larger than the area to which the force of said driving head is applied to a staple, thereby to impede movement of said carrier under a pressure imposed by said end surface on tissue overlying said anvil, which pressure is lower than the driving pressure of said driving head against a staple.

11. The apparatus recited in claim 10, wherein each of said staple retaining units comprises means for retaining and driving a single staple.

12. The apparatus recited in claim 10, wherein said means supporting said carrier comprises cooperative sliding means on said frame and each of said carriers for movement of each carrier relative to the frame in a direction normal to said end surface.

13. The apparatus recited in claim 10, wherein said force transmitting means comprises frictional drag means operative between said staple driving head and said carrier for each of said units.

14. The apparatus recited in claim 10, wherein said force transmitting means comprises compressive elastic means between said driving press and said staple driving head.

15. The apparatus recited in claim 10, including abutment means operative between said staple driving head and said driving press and between said driving head and said carrier after a predetermined amount of relative movement between said carrier, said driving head and said driving press.

* * * * *